United States Patent [19]

Ross et al.

[11] 3,960,500

[45] June 1, 1976

[54] GAS SAMPLING ANALYZING SYSTEM

[75] Inventors: David F. Ross, Euclid; Robert E. Pocock, Highland Heights, both of Ohio

[73] Assignee: Bailey Meter Company, Wickliffe, Ohio

[22] Filed: Jan. 9, 1975

[21] Appl. No.: 539,764

[52] U.S. Cl. .............................. 23/254 E; 23/255 E; 73/23; 73/421.5; 204/1 T
[51] Int. Cl.$^2$ .................... B01K 1/00; G01M 27/26
[58] Field of Search ........... 23/254 E, 255 E, 232 E; 73/23, 421.5; 250/430, 340; 204/1 T, 195 S

[56] References Cited
UNITED STATES PATENTS

| | | | |
|---|---|---|---|
| 2,234,128 | 3/1941 | Miller | 23/232 E |
| 2,807,159 | 9/1957 | Wilson | 73/23 X |
| 3,036,895 | 5/1962 | Cole | 23/255 E X |
| 3,057,693 | 10/1962 | Barnes et al. | 23/254 E X |
| 3,330,960 | 7/1967 | Rich | 23/254 E X |
| 3,558,280 | 1/1971 | Panson et al. | 23/254 E |
| 3,567,394 | 3/1971 | Betz | 23/254 E |
| 3,869,370 | 3/1975 | Sayles | 73/23 X |

Primary Examiner—Robert M. Reese
Attorney, Agent, or Firm—Vytas R. Matas; Joseph M. Maguire

[57] ABSTRACT

A gas sampling analyzing system is provided whereby flue or process gasses are aspirated from a process duct to an analyzer and are therefrom returned back to the process duct to prevent condensation at the system exhaust. The sampling analyzing system is enclosed in an internally heated manifold to prevent condensation of the sampled gas and insure an accurate analysis by the system. The sampling analyzing system has an analyzer assembly connected in parallel with a drop tube with the combination being connected to a sample probe on one side and to a supply air operated aspirator on the other side. The parallel drop tube allows a high flow rate to be maintained between the sample probe and the aspirator to ensure a faster system response to changes in concentrations of the flue or process gasses.

14 Claims, 3 Drawing Figures

GAS SAMPLING ANALYZING SYSTEM

BACKGROUND OF THE INVENTION

1. Field of the Invention

The present invention relates to gas sampling analyzing systems generally and particularly to closed loop gas sampling analyzing systems which return the sample to the area from which the sample was taken.

2. Description of the Prior Art

The control of various processes such as steel making as well as combustion control systems are dependent upon an accurate monitoring and analyzing of process gasses and combustion flue gasses. These gasses are normally analyzed for concentrations of various elements such as $O_2$, $CO$, $CO_2$, $NOx$, $SO_2$, $SO_3$, etc. To obtain such analysis, a sample probe is usually inserted into the flue or other area wherein such gasses are being exhausted and a sample is drawn therefrom. The drawn sample is then passed to an appropriate gas analyzer which provides a reading of the concentration of a certain constituent of the exhaust gas. The analyzed sample is then exhausted to the atmosphere. An example of such prior art systems is disclosed in U.S. Pat. No. 3,512,393 issued to E. L. Weiss, and in U.S. Pat. No. 3,593,023 issued to Michael Dodson et. al.

Since the analyzed exhaust gasses may be noxious and sometimes even toxic, the exhausting of the analyzed gasses as taught by the prior art is impractical and potentially dangerous. Furthermore, since the atmosphere in many instances may be at a temperature below the dewpoint of the sampled gas, condensation may occur at the exhaust line. This condensation causes dust and soot particles in the sample and in the ambient to be deposited in the exhaust line initially restricting and eventually plugging the exhaust line and making the system inoperable.

The prior art devices also cause problems when mounted to ducts to sample gasses therefrom. Since the static pressure in the duct conveying the exhaust gasses varies, the flow through the prior art analyzers also varies causing inaccurate readings.

The prior art analyzing systems described above also have a relatively slow reaction time to a change in the concentration of elements in the exhaust gasses. This is primarily due to the small amount of sample gas that is drawn by the probe and conveyed to the analyzer. The change in concentration is not detected until the sample gas is slowly conveyed to the analyzer from the probe and its associated connecting lines.

SUMMARY OF THE INVENTION

The present invention solves the previously discussed problems of the prior art systems as well as other problems by providing a unique closed loop sampling and analyzing system which exhausts the sampled and analyzed gas back to the same area from which the sample was drawn. This is accomplished by sealably mounting a sample probe and an exhaust line of the system to a duct containing exhaust gasses. The sample probe draws a sample of the gasses from the duct and conveys the sample to an analyzer assembly which establishes a control signal indicative of the concentration of a certain element in the sample gas. The analyzer assembly is connected to an aspirator which draws the analyzed sample from the analyzer assembly and conveys it to the exhaust line which exhausts the sample gas back into the duct where it may be exhausted along with the duct exhaust gasses.

As such the present invention solves the problem associated with devices which exhaust potentially dangerous sample gasses into a closed ambient external of the duct where people may be present. The present invention has other advantages since both the inlet and the outlet of the sampling analyzing system of the present invention are connected to the same duct. Any static pressure changes in the duct will not affect the flow of sample gas through the system since the flow is determined only by the additive pressure that the aspirator adds to the static pressure of the duct. Also, since the exhaust of the system of the present invention is connected to the same duct from which the sample was drawn, there is little likelihood of condensation occurring at the exhaust of the system, as in known prior art systems. Thus the system of the present invention will not plug up at the exhaust from soot and dirt being condensed out to block the exhaust.

The analyzer assembly of the present invention is also uniquely constructed to provide a faster reaction time to changes in concentration of duct exhaust gasses than prior art devices. The analyzer, which is usually an electrochemical cell, is parallel connected with a drop tube. This parallel combination is connected to the sample probe on one side and to the aspirator on the other side. This unique connection allows an increased flow of sample gas to be drawn through the sampling analyzing system while still forcing the proper amount of sample to flow through the analyzer. Thus the flow of sample gas through the present system is not limited by the size of the analyzer cell as in the prior art devices.

The system of the present invention is also uniquely constructed to prevent any condensation from occurring within the sampling analyzing system. The system is enclosed within a thermostatically controlled manifold which maintains the system at a temperature above the dewpoint of the sample gas. The supply air which operates the aspirator is connected to the system by a sinusoidal connecting line mounted within the heated manifold. The connecting line therefore preheats the supply air before it is applied to the aspirator. Condensation from cold supply air mixing with the induced sample gas is thereby effectively prevented.

From the foregoing it will be seen that one aspect of the present invention is to provide a closed loop sampling analyzing system which will draw and exhaust sample gas from and to the same duct to provide a safe system which will be insensitive to duct static pressure variations and which will not allow condensation at the system exhaust.

Another aspect of the present invention is to provide a sampling analyzing system which will have a faster reacton time to concentration changes in duct exhaust gasses.

Yet another aspect of the present invention is to provide a sampling analyzing system which will prevent condensation from occurring anywhere within the system, including the supply air connection to the aspirator.

These and other aspects of the present invention will be more clearly understood after a review of the following description of the preferred embodiment of the invention when considered in conjunction with the drawings.

DESCRIPTION OF THE PREFERRED EMBODIMENT

Figure 1:
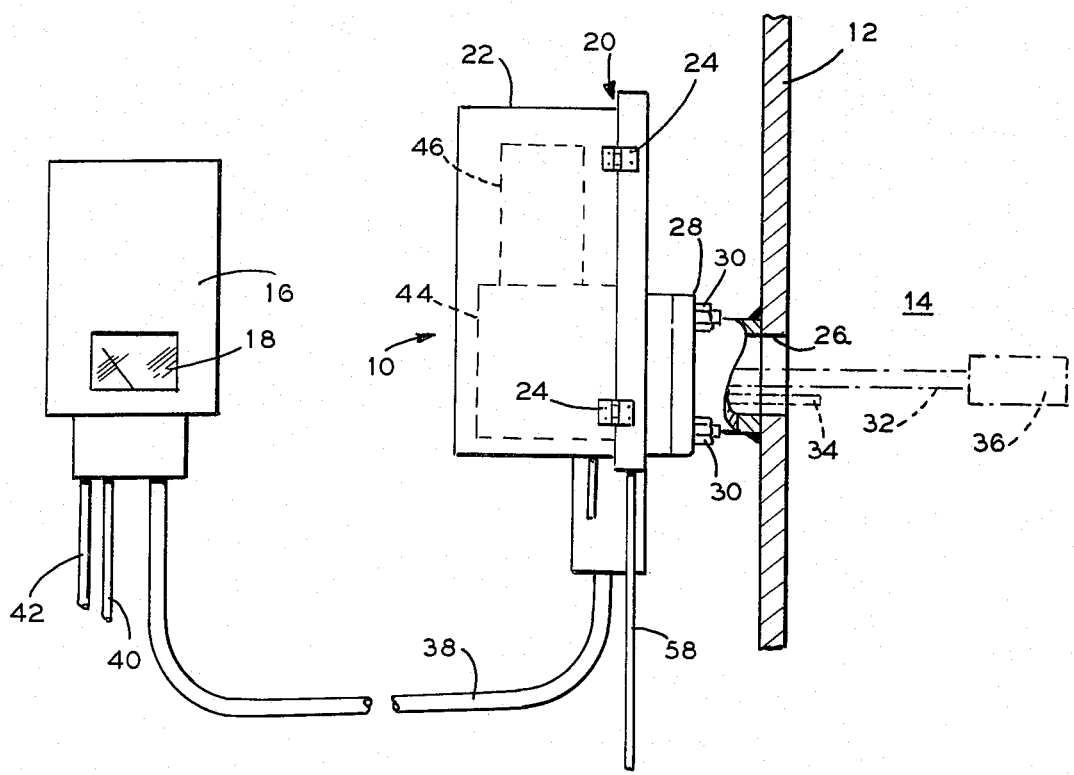
FIG. 1 is a representation of the sampling analyzing system of the present invention being mounted on a duct.

Referring now to the drawings, it will be understood that the showings therein are for the purposes of illustrating a preferred embodiment of the present invention and the invention is not limited thereto.

As may be best seen with reference to FIG. 1, a sampling analyzing system 10 is mounted to a duct or boiler wall 12 to draw process gas 14 from inside the duct and exhaust it back thereto after analyzing the process gas 14. The sampling analyzing system 10 is controlled by a control station 16 which may have an indicator 18 for displaying the measured concentration of a particular element in the process gas 14, such as the concentration of oxygen.

The sampling analyzing system 10 is enclosed within an insulated enclosure 20-having a door portion 22 which is opened by releasing a known latch assembly 24 to provide ready access to the components therein. The sampling analyzing system 10 is mounted to the duct or boiler wall 12 through a pipe nipple 26 which is welded to the duct 12 and which has a pipe mounting flange 28. The enclosure 20 of the sampling analyzing system 10 is attached to the flange 28 by nut and bolt assemblies 30 to thereby provide a sampling analyzing system 10 which is readily removable. Process gasses are drawn into the sampling analyzing system 10 through a sample probe 32 which extends into the duct and are exhausted back into the same duct by an exhaust line 34 to prevent condensation at the exhaust. The end of the probe 32 is covered with a probe filter 36 which prevents dust and soot particles from being entrained by the probe 32 and therefrom by the sampling analyzing system 10. Electrical power is provided to the sampling analyzing system 10 from the control station 16 by a flexible conduit 38 which also transmits a signal indicative of measured gas concentration from the sampling analyzing system 10 to the control station 16. The control station 16 may modify the received signal and transmit it to a process controller along line 40 to adjust the process producing the exhaust gasses in the duct. The control station 16 is powered through a main power supply connection 42.

Figure 2:
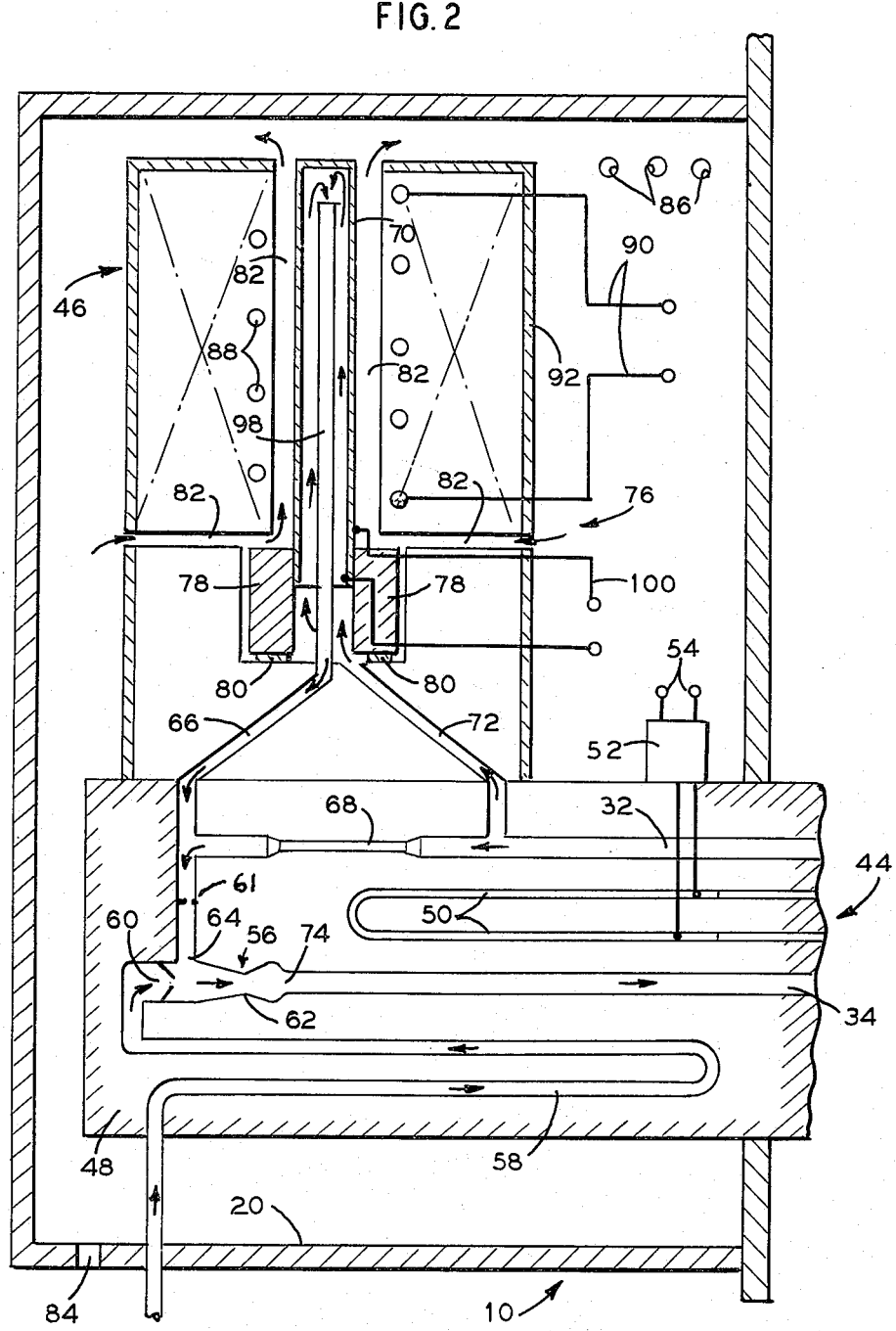
FIG. 2 is a detailed representation of the sampler analyzer of the system of FIG. 1.

Referring now to FIG. 2 it may be seen that the sampling analyzing system 10 of the present invention has a sampling assembly 44 which draws a sample of the process gasses 14 from the duct, transmits the sample to an analyzer assembly 46, and draws the analyzed sample back to the sampling assembly 44 to be exhausted therefrom back into the duct. By exhausting the sample back into the hot duct from which the sample was drawn, condensation which may occur when the sample is exhausted into an ambient below the dewpoint of the sample is effectively prevented. The sampling assembly 44 includes a manifold 48 which is heated by a resistance heater 50 to prevent condensation of the sample from occurring anywhere within the sampling assembly 44. The resistance heater 50 is thermostatically controlled by a thermostat 52 to maintain the manifold 48 at approximately 400°F which is a temperature substantially above the dewpoint temperature of the sample drawn from the duct, in this embodiment $O_2$. The thermostat 52 is a well known bi-metal device which prevents the application of electrical power to the resistance heater 50 along lines 54 whenever the bi-metal senses a 400°F temperature. Power is supplied to the lines 54 through wiring internal of the control station 16 connecting the power line 42 along the conduit 38 to the lines 54 (not shown).

The sample is drawn into the sampling assembly 44 from the probe 32 by the action of an aspirator assembly 56 formed within the manifold 48. The aspirator assembly 56 is powered by a main air supply which is connected to the aspirator assembly 56 by a connecting line 58 also formed within the manifold 48 as a series of sinusoidal paths. The connecting line 58 is made sinusoidal to provide a longer contact time of the supply air with the heated manifold 48. This is done to preheat the supply air before it contacts the aspirator 56 to thereby prevent condensation from occurring with the drawn sample when the two are mixed in the aspirator 56 since the supply air may be at a temperature lower than the dewpoint of the drawn sample.

The aspirator assembly 56 has a power inlet nozzle 60 connected to the connecting line 58 to supply preheated supply air flow through a restriction 62 to thereby produce a negative pressure at a sample gas inlet 64. The nozzle 60 is sized to maintain a substantially constant induced flow into the aspirator 56. This is accomplished by operating a nozzle 61 in the critical area for fixed flow through the nozzle 60. The inlet 64 is connected to an outlet 66 of an electrochemical cell analyzer 70 of the analyzing assembly 46 to draw the analyzed gas therefrom. The inlet 64 is also connected to a drop tube 68 which is parallel connected across the analyzer 70 through its connection to an inlet 72 of the analyzer 70 and the outlet 66 of the analyzer 70. The drop tube 68 is a restricted passageway which is sized with respect to the passageways provided by the analyzer 70 to distribute the flow induced by the negative pressure at the aspirator inlet 64 in a ratio of approximately 5/1 between the drop tube 68 and the analyzer 70. This allows a greater quantity of sample gas to be drawn from the sample probe 32 by the aspirator assembly 56 than would be ordinarily possible if all of the sample gas were drawn exclusively through the analyzer 70. This increased quantity of sample gas decreases the time delay in transporting the sample to the analyzer 70 through the sample probe 32 and increases the sensitivity of the analyzer 70 to any changes in process gas 14 concentrations. The sample gas drawn in by the aspirator assembly 56 along with the supply air is exhausted from an aspirator outlet 74 into the exhaust line 34 and therefrom back into the same duct from which the sample was drawn.

The analyzer assembly 46 includes a manifold 76 which is mounted to the manifold 48 to connect the analyzer outlet 66 and the analyzer inlet 72 across the drop tube 68 and to connect the analyzer outlet 66 to the sample gas inlet 64 of the aspirator assembly 56. The analyzer 70 may be a well known Zirconium-Oxide oxygen analyzer formed as a tubular member having one open end. The open end is mounted within the manifold 76 through a support block 78 and a seal gasket 80. The sealed mounting maintains a seal between the inside and the outside of the analyzer 70. The outside of the analyzer 70 is open to the ambient air of the enclosure 20 by allowing the circulation of air through passageways 82 to thereby maintain reference air on the outside of the analyzer 70. This reference air is supplied to the inside of the enclosure 20 through an inlet 84 and is exhausted from the enclosure 20 through vent holes 86 formed in the enclosure 20. Since the analyzer 70 must be maintained at approximately 1500°F operating temperature, circumferential heater coils 88 are placed in the manifold 76 around the analyzer 70 to maintain the analyzer 70 at the operating temperature. The heater 88 is powered and controlled by electrical connecting lines 90 which are contained in the conduit 38 to connect the heater 88 to the power cord 42 in the control station 16. The manifold 76 is enclosed by thermal insulation 92 to insulate the ambient of the enclosure 20 from the high temperature of the manifold 76 to prevent any harm to the electrical connections and other components contained therein which are usually rated for lower temperature operation.

Figure 3:
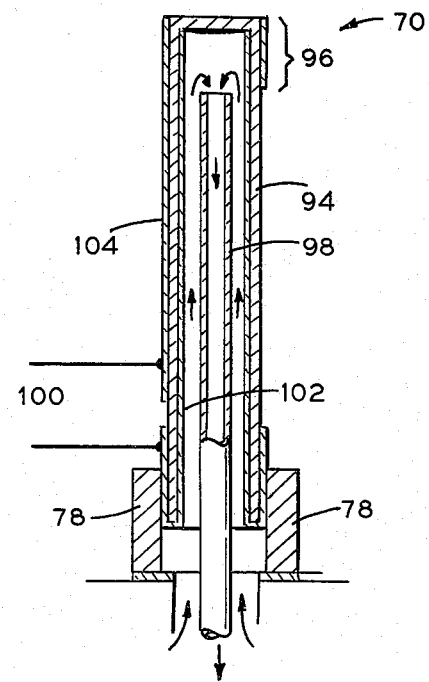
FIG. 3 is a detailed representation of the electrochemical cell of the present invention.

As may be best seen with reference to FIG. 3, the analyzer 70 in the preferred embodiment is a well known oxygen analyzer formed as an open ended Zirconium-Oxide tube 94 having an analysis zone 96 at the closed end of the tube 94. An exhaust tube 98 is mounted internally of the tube 94 to exhaust the analyzed sample from the analysis zone 96. Sample gas is drawn from the open end of the tube 94, which is connected to the analyzer inlet 72, and along the length of the tube 94 into the analysis zone 96 by the negative pressure induced at the analyzer outlet passage 66 through its connection to the exhaust tube 98. The outside of the analysis zone 96 is maintained open to the reference air having a known oxygen concentration. The analyzer 70 establishes an electrical output signal across the tube 94 in response to a variation of the oxygen concentration in the sample gas according to the Nernst equation:

$$E(mv) = RT/nF \ln (P_x/P_r)$$

$E(mv)$ = sensor output
$R$ = perfect gas constant
$T$ = temperature, degrees Kelvin
$n$ = number of electrons transferred in stoichiometric equation
$F$ = Faraday's constant
$P_x$ = partial pressure of oxygen in unknown or sample gas
$P_r$ = partial pressure of oxygen in reference air The electrical signal established across the tube 94 is picked up by a pair of electrical conductors 100. One of the conductors 100 is electrically connected to the sample side of the analysis zone 96 by a platinum film 102 extending along the inside of the tube 94 while the other is connected to the reference side 104 of the analysis zone 96 by a platinum film extending along the outside of the tube 94. The conductors 100 extend through the conduit 38 to the control station 16 to conduct the control signal thereto where it may actuate the indicator 18 before being further conducted along the signal line 40 to initiate a control function in the process which would change the oxygen concentration in the process gas 14.

Certain modifications and additions will occur to those skilled in the art upon consideration of the foregoing description. It should be understood that such modifications and additions have been deleted for the sake of conciseness and readability but that they are properly included within the scope of the present invention.

What is claimed as new and desire to secure by Letters Patent of the U.S. is:

1. A gas sampling analyzing system for analyzing gasses within a duct comprising:
   probe means, mountable within the duct, to draw a sample of the gasses therein;
   an analyzer assembly mounted outside of the duct and being connected to said probe means to analyze said sample;
   an exhaust line connected to said analyzer assembly for exhausting the analyzed gas from said analyzer assembly back to the duct; and
   aspirator means mounted externally of the duct for inducing a substantially constant flow of sample gas from the duct to said probe means to said analyzer assembly and through said exhaust line back to the duct.

2. A gas sampling analyzing system for analyzing gasses within a duct comprising:
   probe means, mountable within the duct, to draw a sample of the gasses therein;
   an analyzer assembly mounted outside of the duct and being connected to said probe means to analyze said sample including a gas analyzer for providing an electrical signal in response to said sample being applied thereto and a drop tube connected in parallel with said gas analyzer to bypass a portion of said sample from said gas analyzer to thereby increase the flow through said probe means;
   an exhaust line connected to said analyzer assembly for exhausting the analyzed gas from said analyzer assembly back to the duct; and
   means mounted externally of the duct for inducing a substantially constant flow of sample gas from the duct to said probe means to said analyzer assembly and through said exhaust line back to the duct.

3. A gas sampling analyzing system as set forth in claim 2 wherein said inducing means includes an aspirator having an inlet connected to said gas analyzer, and to said drop tube to induce the flow of said sample from said probe means to said drop tube and said gas analyzer, said aspirator having an outlet connected to said exhaust line to exhaust said sample from said gas analyzer and said drop tube to the duct.

4. A gas sampling analyzing system for analyzing gasses within a duct comprising:
   probe means, mountable within the duct, to draw a sample of the gasses therein;
   an analyzer assembly mounted outside of the duct and being connected to said probe means to analyze said sample;
   an exhaust line connected to said analyzer assembly for exhausting the analyzed gas from said analyzer assembly back to the duct;
   means mounted externally of the duct for inducing a substantially constant flow of sample gas from the duct to said probe means to said analyzer assembly and through said exhaust line back to the duct;
   manifold means for encasing said analyzer assembly and said inducing means; and
   heating means mounted within said manifold means for maintaining said analyzer assembly and said inducing means as a temperature above the dewpoint of said sample.

5. A gas sampling analyzing system as set forth in claim 4 wherein said inducing means includes:
   an air supply system;
   an aspirator connected to said air supply system to be powered therefrom; and
   a connecting line formed within said manifold assembly and connecting said air supply to said aspirator, said connecting line being heated by said heating means to preheat the air supplied to said aspirator to a temperature above the dewpoint of said sample.

6. A gas sampling analyzing system as set forth in claim 5 wherein said aspirator includes:
   an inlet connected to said analyzer assembly;
   a nozzle formed within said inlet to maintain a substantially constant flow of said sample from said analyzer assembly to said aspirator in response to a change in differential pressure across said nozzle.

7. A gas sampling analyzing system for analyzing the composition of flue exhaust gasses comprising:
   a sample probe sealably mounted in the flue for drawing exhaust gasses therefrom;
   an electrochemical cell connected to said sample probe for analyzing exhaust gasses and establishing an electrical signal in response to a particular concentration of exhaust gasses;
   an aspirator having an inlet connected to said electrochemical cell to induce the flow of exhaust gasses from said sample probe to said electrochemical cell and having an outlet connected to the flue to exhaust the exhaust gasses from said electrochemical cell back to the flue in response to the flow of supply air through said aspirator; and
   an air supply connected to said aspirator to provide a flow of supply air therethrough.

8. A gas sampling analyzing system as set forth in claim 7 including a by-pass tube connected across said electrochemical cell to increase the flow of exhaust gasses from said sample probe to said aspirator for providing a faster reaction time of said electrochemical cell to a change in the concentration of the exhaust gasses.

9. A gas sampling analyzing system as set forth in claim 7 including manifold means for enclosing said electrochemical cell and said aspirator and further including heating means mounted within said manifold means to maintain said electrochemical cell and said aspirator at a temperature above the dewpoint of the exhaust gasses flowing therethrough.

10. A gas sampling analyzing system as set forth in claim 9 including a connecting line formed within said manifold for supplying air from said air supply to said aspirator and wherein said heating means preheats the air in said connecting line to a temperature above the dewpoint of the exhaust gasses to prevent condensation from occurring in said aspirator.

11. A gas sampling analyzing system as set forth in claim 10 wherein said electrochemical cell includes a Zirconium-Oxide oxygen analyzer establishing an electrical output signal proportioned to the ratio of the oxygen concentration in a known sample to the oxygen concentration in the exhaust gasses.

12. A gas sampling analyzing system as set forth in claim 11 wherein said manifold includes a first area having said oxygen analyzer mounted therein and a second area having said connecting line and said aspirator formed therein, and wherein said heating means includes a first heater for maintaining said first area at a first temperature and a second heater for maintaining said second area at a second temperature less than said first temperature.

13. A gas sampling analyzing system as set forth in claim 12 wherein said first heater maintains said first area at substantially 1500°F and said second heater maintains said second area at substantially 400°F.

14. A gas sampling analyzing system as set forth in claim 13 including an enclosure for enclosing said manifold, said enclosure having an inlet for supplying reference air to said enclosure, said manifold having a passageway formed in said first area to provide flow of reference air from said enclosure to said oxygen analyzer.

* * * * *